(12) United States Patent
Briquet et al.

(10) Patent No.: US 6,406,792 B1
(45) Date of Patent: Jun. 18, 2002

(54) BIOCOMPATIBLE COATINGS

(75) Inventors: Francois Jean Briquet, Nice; Gary Lord, Roquefort les Pins, both of (FR)

(73) Assignee: Dow Corning France S.A., Valbonne (FR)

( * ) Notice: Subject to any disclaimer, the term of this patent is extended or adjusted under 35 U.S.C. 154(b) by 0 days.

(21) Appl. No.: 09/464,903

(22) Filed: Dec. 15, 1999

(30) Foreign Application Priority Data

Dec. 23, 1998 (EP) .............................. 98480093

(51) Int. Cl.$^7$ ............................... B32B 26/20
(52) U.S. Cl. .................. 428/447; 524/858; 524/860; 524/492; 528/14; 528/34; 424/422
(58) Field of Search .................. 524/858, 860, 524/492, 27; 528/14, 34; 424/422; 428/447

(56) References Cited

U.S. PATENT DOCUMENTS

| | | | |
|---|---|---|---|
| 3,574,673 A | 4/1971 | Schweiger | 117/132 |
| 4,656,083 A | 4/1987 | Hoffman et al. | 428/265 |
| 4,678,468 A * | 7/1987 | Hiroyoshi | |
| 4,692,347 A | 9/1987 | Yasuda | 477/40 |
| 4,720,521 A | 1/1988 | Spielvogel et al. | 524/862 |
| 5,053,048 A | 10/1991 | Pinchuk | 623/1 |
| 5,061,738 A | 10/1991 | Solomon et al. | 523/100 |
| 5,091,483 A * | 2/1992 | Mazurek et al. | |
| 5,224,958 A | 7/1993 | Warunek et al. | 623/11 |
| 5,326,584 A | 7/1994 | Kamel et al. | 427/491 |
| 5,451,428 A | 9/1995 | Rupp | 427/2.12 |
| 5,534,588 A * | 7/1996 | Knepper et al. | |
| 6,180,249 B1 * | 1/2001 | Stein | |

FOREIGN PATENT DOCUMENTS

| | | | |
|---|---|---|---|
| EP | 0309345 A1 | 9/1988 | A61L/33/00 |
| EP | 0331774 A1 | 9/1989 | A61L/27/00 |
| EP | 0309345 B1 | 9/1993 | A61L/33/00 |
| EP | 0651005 A1 | 3/1995 | C08J/7/04 |
| EP | 0748848 A2 | 6/1996 | C08L/3/07 |
| WO | 95/20688 | 8/1995 | C23C/16/04 |

OTHER PUBLICATIONS

Matsusawa, Y.; Yasuda, H. Semi–continuous Plasma Polymerization Coating Applied onto the Inside Surface of Plastic Tubing (1982) pp. 65–74 Journal of Applied Polymer Science; Applied Polymer Symposium 38 (1984).
Semi–Continuous Plasma Polymerization Coating Applied onto the Inside Surface of Plastic Tubing—Y. Matsuzawa and H. Yasuda.

* cited by examiner

Primary Examiner—Robert Dawson
Assistant Examiner—Kuo-Liang Peng
(74) Attorney, Agent, or Firm—Roger E. Gobrogge

(57) ABSTRACT

A medical device has a biocompatible coating made by reacting a reactive polysiloxane, an acetoxysilane crosslinking agent, a reinforcing silica and a metal catalyst. Such devices cause decreased reactions when they come into contact with a human or animal body or its blood, fluids or other biological membranes.

16 Claims, No Drawings

BIOCOMPATIBLE COATINGS

The present invention relates to methods of coating surfaces to render them substantially biocompatible and to the biocompatible surfaces produced thereby. These coatings are especially valuable on medical devices.

Biocompatible surfaces are important for medical devices. The term 'biocompatible surface' is used herein to mean a surface which causes either no or a minimal reaction when it comes into contact with a human or animal body or its blood, fluids or other biological membranes. The term 'medical device' is used herein to encompass all medical apparatuses which are used in the treatment of, and come in contact with, a human or animal body or its blood, fluids or other biological membranes. Such medical devices include, for example, implants, prostheses and components used in the delivery or routing of blood or fluids.

When medical devices have non-biocompatible surfaces, they can initiate a reaction by the human or animal body or its blood, fluids or other biologic membranes which may result in serious patient complications such as rejection or post perfusion syndromes. Medical devices have, therefore, conventionally been made of relatively inert plastic or elastomeric materials. These materials, however, have varying degrees of biocompatibility.

Since the biocompatibility of medical devices is generally a result of their surface properties, changing the surface composition, for example by applying or grafting on more biocompatible material, may enhance their bioperformance and improve the patient outcome.

Attempts have been made to improve the surface properties of medical devices. For instance, it is well known to coat the surface of medical devices such as needles with polydimethylsiloxanes for lubrication. In the absence of further treatment (e.g., heat), these polydimethylsiloxanes could migrate from the surface to which they are applied.

U.S. Pat. No. 3,574,673 teaches the use of organosiloxane polymers which can be cured on various surfaces such as needles to provide a lubricating film. The organosiloxane polymers used in this reference comprise aminosiloxane units and organosiloxane units which cure in the presence of moisture to form the film. These organosiloxane polymers, however, require moisture for curing and take a substantial time to cure.

Similarly, U.S. Pat. No. 4,720,521 teaches coating devices such as needles or catheters with a curable silicone composition to form a crosslinked, adherent coating which serves as a matrix for a non-reactive lubricating silicone polymer. The curable silicone composition used in this reference comprises a siloxane polymer which has two or more vinyl groups, a siloxane which has two or more pendant hydrogen atoms, a siloxane chain extending polymer having two or more terminal hydrogen atoms and a platinum catalyst. The coatings of the reference, however, are disadvantageous because of their complex nature and because of the curing techniques.

U.S. Pat. No. 5,061,738 also teaches a blood compatible, lubricious composition for use on medical articles. The composition comprises a quaternary ammonium complex of heparin and a silicone. The silicones disclosed in the composition, however, are not cured and, thus, could migrate from the surface to which they are applied.

We have now discovered a coating that can render a medical device biocompatible without the problems of the prior art.

The present invention relates to a medical device having a biocompatible coating, said biocompatible coating comprising the reaction product of a composition comprising a reactive polysiloxane, an acetoxysilane crosslinking agent, a reinforcing silica and a metal catalyst.

The medical devices which can be coated by the present invention can be any of the known medical apparatuses which are likely to come into contact with a human or animal body or its blood, fluids or other biological membranes. These include, for example, implants and prosthetics such as cardiac valves, shunts, implanted tubes, and the like. It also includes, for example, components of extracorporeal circulation or fluid delivery such as tubing, valves, pumps, cannulas, catheters, needles and the like.

The above medical devices can be made of nearly any material which is suitable for the application. This includes, for example, plastics, elastomers, metals and the like. Specific materials include polyvinylchlorides (PVC), polycarbonates (PC), polyurethanes (PU), polypropylenes (PP), polyethylenes (PE), silicones, polyesters, polymethylmethacrylate (PMMA), hydroxyethylmethacrylate, N-vinyl pyrrolidones, fluorinated polymers such as polytetrafluoroethylene, polyamides, polystyrenes, copolymers or mixtures of the above polymers and medical grade metals such as steel or titanium. Preferred materials include silicones, PVCs, PCs, PUs, PPs, PEs and PMMA.

The medical device made of the above materials is coated with the biocompatible coating of the invention. The entire device may be coated with this coating or, alternatively, just that portion of the device that comes into contact with the human or animal body or its blood, fluids or other biological membranes can be coated.

The biocompatible coating of the invention is the reaction product of a composition comprising a reactive polysiloxane, an acetoxysilane crosslinking agent, a reinforcing silica and a metal catalyst.

The reactive polysiloxane can be nearly any which reacts with the acetoxysilane crosslinking agent to cure and form the biocompatible coating. Such polysiloxanes generally have reactive groups such as hydrogen, hydroxyl, alkoxy or alkoxyalkoxy bound to silicon in the polymer. As such, the reactive polysiloxanes generally have siloxane units of the general structure:

$$R_m R^1 SiO_{(3-m)} \qquad \qquad I$$

in which each R represents a monovalent hydrocarbon group having up to 20 carbon atoms such as an alkyl (e.g., methyl, ethyl, propyl or butyl) or phenyl groups, m is 1 or 2 and $R^1$ represents a hydrogen, a hydroxyl (OH) group or an alkoxy group (OR) such as methoxy, ethoxy, propenyloxy and the like. Preferably, R is methyl and $R^1$ is hydroxyl.

The reactive polysiloxanes can, and preferably does, also have other units such as, for example, units of the general structure:

$$R_n SiO(4-n) \qquad \qquad II$$

in which R is as above, and n is 0, 1, 2 or 3. In addition, or alternatively, the polysiloxane can also contain, for example, organic groups such as acrylates, carbonates, polybutylenes or the like.

The reactive polysiloxane can also comprise mixtures or copolymers of the above polysiloxanes. Obviously, however, the polysiloxane must have at least one, preferably at least two, units of formula I for crosslinking.

In a preferred embodiment of the invention, the reactive polysiloxane comprises a polysiloxane having the structure.

$$OH(Si(CH_3)_2O)_x H \qquad \qquad III$$

wherein x is an integer of 3 to 10,000 or more.

The reactive polysiloxanes can have a wide variety of viscosities such as from about 10 mm²/s to gums (e.g., viscosities up to 50 million mm²/s) at 25° C. Such polysiloxanes generally have number average molecular weights (Mn) of up to 500,000 or more.

Preferably, the reactive polysiloxane is of Formula III wherein x is an integer which results in a siloxane gum. More preferably, the reactive polysiloxane has a viscosity of 500,000 to 50 million mm²/s at 25° C. Most preferably, the reactive polysiloxane has an Mn of about 250,000 to 350,000.

The acetoxysilane crosslinking agent of the present invention comprises a material or a mixture of materials of the structure $$R^2{}_{4-b}SiR^3{}_b$$

in which $R^2$ is a monovalent hydrocarbon group having up to 20 carbon atoms such as an alkyl (e.g., methyl, ethyl, propyl or butyl) or a phenyl group, $R^3$ is an acetoxy group, and b is 2, 3, or 4. In addition, the hydrolysis and condensation products of these silanes such as, for example, polysiloxanes containing the above acetoxy groups are also functional herein.

Examples of specific acetoxysilanes include methyltriacetoxysilane, ethyltriacetoxysilane and mixtures thereof.

The crosslinking agents are used in amounts of about 10 ppm to 10 wt % based on the weight of the polysiloxane. Preferably, the amount of crosslinking agent is sufficient to provide a ratio of reactive groups on the polysiloxane to acetoxy groups of 0.1 to 10 and more preferably 0.5 to 2.

The metal catalysts suitable for use in the present invention are known in the art and may include, for example, organic metal compounds such as organotin salts. Examples of catalysts include stannous octoate, dibutyltin dilaurate, dibutyltin diacetate, dimethyltin dineodecanoate, dibutyltin dimethoxide, isobutyl tin triceroate, dimethyltin dibutyrate, dimethyltin dineodecanoate, triethyltin tartrate, tin oleate, tin naphthenate, tin butyrate, tin acetate, tin benzoate, tin sebacate, and tin succinate. Generally, these catalysts are used in amounts of between about 0.001 and 10 wt. % based on the weight of the composition.

The present invention also comprises a reinforcing filler. Such fillers are known in the art and generally comprise those conventionally found in silicone elastomers. They include, for example, precipitated or fumed silicas which may be pre-treated or treated in situ to render them hydrophobic ground quartz, titania, zirconium silicate, ferric oxide, aluminum oxide, calcium carbonate and mixtures thereof. Preferably, the filler is silica such as reinforcing amorphous silica (pyrogenic or fumed) with 50–300 m²/g surface area, preferably 120–200 m²/g, untreated or treated with silanes (e.g. trimethylchlorosilane), silazane (e.g. hexamethyldisilazane) or low molecular weight polysiloxane or mixtures thereof.

The fillers are used in an amount sufficient to provide the desired properties. Generally, this is an amount of about 0.1 to 100 parts per hundred parts of the polysiloxane.

If desired, the formulation of the present invention may contain additional ingredients such as colorants, coloured indicators, diluents, extenders, for example silicone fluids, silicone resins, excipients employed in pharmacy, stabilisers, or surfactants, and processing aids such as cyclic or linear polydiorganosiloxanes.

One particularly advantageous optional ingredient in the formulation of the present invention is a diluent. Such diluents are often necessary to decrease the viscosity of the silicones sufficiently to permit application.

Examples of diluents include silicon containing materials such as hexamethyldisiloxane, octamethyltrisiloxane, and other short chain linear siloxanes, cyclic siloxanes such as octamethylcyclotetrasiloxane and decamethylcyclopentasiloxane, organic materials such as alkanes or any other material or mixture of materials which can dilute the formulation without affecting any of the components of the formulation.

The above diluents are often used in amounts of between about 20 and 99.9 wt %, preferably from 85 to 99 wt. W. On application, however, the diluent often volatilizes leaving the other components on the desired site.

Yet another advantageous optional ingredient is an anticoagulant. These materials are known in the art. One particularly preferred anticoagulant is heparin. If used, heparin is included in an amount insufficient to inhibit coagulation but sufficient to enhance the material's biocompatibility, generally in a range of between about 10 ppm and 1 wt. % based on the weight of the final composition, excluding any diluent (e.g. cured elastomer).

If heparin is used, it can be in any form desired such as a salt selected from, for example, ammonium, benzalkonium, calcium, lithium, and zinc, as a derivative of low molecular weight heparin fragments, or as heparin-like polyanions such as dermatan sulfate, heparan sulfate and their derivatives.

Other anticoagulants useful herein include, for example, a prostaglandin, urokinase, streptokinase, tissue plasminogen activator and hirudin used in amounts insufficient to inhibit coagulation but sufficient to enhance the material biocompatibility.

Mixing of the components of the invention causes curing in the presence of adequate moisture. As such, the components are often stored in separate containers prior to use or they are mixed and stored in containers which exclude moisture. For instance, one container could contain the catalyst and a second could contain the reactive polysiloxane and the acetoxysilane. Alternatively, the catalyst could be mixed with the reactive polysiloxane in one container and the acetoxysilane could be in a second container. The filler and optional ingredients could be included in either or both of the parts depending on factors such as stability, viscosity, and interactions.

The composition of the present invention is then mixed and applied to the medical device. The method of applying can be, but is not limited to, dip coating, spray coating or flow coating. Other coating techniques, however, are also deemed to be within the scope of this invention.

The diluent, if used, is then allowed to evaporate leaving the cured composition. If desired, the coated device can be heated or radiated to facilitate the cure. Heating can be at temperatures of 50° C. to 120° C. for several minutes up to several hours, depending on the heat stability of the substrate.

The resultant device has a thin, adherent silicone coating which renders it biocompatible. The coating can have a variety of thicknesses such as from about several nanometers up to several millimeters, preferably 0.1 to 10 micrometers.

In order that the invention may become more clear there now follows examples which are illustrative of the invention. Unless indicated, all parts are by weight and all viscosities are at 25° C.

EXAMPLE 1

A coating composition A was made by mixing 95 wt. % hexamethyldisiloxane with 4.9 wt. % of a composition comprising 1 wt. treated silica, 6 wt. % silanol terminated polydimethylsiloxane gum having a viscosity of about 30 million mm²/s at 25° C. and 93 wt. % hexamethyldisiloxane. The resulting composition was then mixed with 0.1 wt % of a composition comprising 1 wt. % dibutyl tin diacetate and 99 wt. % of a methyl-ethyl triacetoxysilane mixture.

Medical grade polycarbonate was injection moulded into two slabs with dimensions of 44×10×1 mm (test samples I). Medical grade polycarbonate loaded with a TiO₂ filler was also injection molded into two slabs with dimensions of 44×10×1 mm (test samples II).

Solutions of the above coating composition A were coated on one slab of test sample I and one slab of test sample II by immersion for a few seconds followed by allowing the coating composition to cure for 24 hours at 25° C. in air. One slab of test sample A and one slab of test sample B were left uncoated as controls.

Biocompatibility was tested by contacting the test sample slabs with human blood from 3 donors and measuring clotting time and protein (fibrin) and platelet adhesion. Determination of the clotting time assesses globally the activation of the coagulation cascade which is a key parameter when it comes to evaluate hemocompatibility of a material. The higher the clotting time, the lower the coagulation activation, thus the higher material compatibility.

Platelet and fibrin adhesion was measured by scanning electronic microscopy (SEM) at 40× to 10,000×, after 1, 3 and 7 min of blood contact. Both events are mainly responsible for initiating the coagulation cascade. The lower the % of coverage the lower the blood activation, thus the higher the biomaterial hemocompatibility. The results are summarized in Tables 1 and 2.

TABLE 1

Clotting Time.

| Substrate | Average Clotting Time (% of control) |
|---|---|
| Test sample I (PC) with coating composition A | 174 |
| Test sample I (PC) control | 100 |
| Test sample II (TiO₂PC) with coating composition A | 139 |
| Test sample II (TiO₂PC) control | 100 |

TABLE 2

SEM evaluation of platelet and fibrin Adhesion.

| Material Adhesion | Exposure Time (min) | Surface Covering | | | Platelet Adhesion | | | Fibrin | | |
|---|---|---|---|---|---|---|---|---|---|---|
| | | Donor 1 | Donor 2 | Donor 3 | Donor 1 | Donor 2 | Donor 3 | Donor 1 | Donor 2 | Donor 3 |
| Test sample I (PC) control | 3 | 1 | 2 | 1 | 2 | 3 | 2 | 1 | 1 | 1 |
| Test sample I (PC) control | 5 | 2 | 4 | 5 | 3 | 2 | 3 | 2 | 3 | 4 |
| Test sample I (PC) control | 7 | 3 | 3 | 3 | 3 | 3 | 3 | 3 | 4 | 3 |
| Test sample I (PC) with coating composition A | 3 | 1 | 1 | 1 | 0 | 1 | 1 | 0 | 0 | 1 |
| Test sample I (PC) with coating composition A | 5 | 1 | 1 | 2 | 1 | 1 | 1 | 0 | 0 | 0 |
| Test sample I (PC) with coating composition A | 7 | 2 | 2 | 1 | 1 | 1 | 0 | 1 | 1 | 0 |

Surface Covering
0 = 0%
1 = 0–20%
2 = 20–40%
3 = 40–60%
4 = 60–80%
5 = 80–100%
Platelet & Fibrin Adhesion
0 = none
1 = discrete
2 = moderate
3 = marked
4 = severe

EXAMPLE 2

A coating composition (B) was made by mixing (I) 94,4 wt. % hexamethyldisiloxane, (II) 0.6 wt. O of a solution comprising 2 wt. % benzalkonium heparin and 98 wt. % ethanol, (III) 4.9 wt. % of a composition, comprising 1 wt. % treated silica, 6 wt. % silanol terminated polydimethylsiloxane gum having a viscosity about 30 million mm²/sec at 25° C. and 93 wt. % hexamethyldisiloxane and (IV) 0.1 wt % of a composition comprising 1 wt % dibutyl tin diacetate and 99 wt. % of a methyl-ethyl triacetoxysilane mixture to obtain the coating composition B.

Medical grade polycarbonate slabs prepared as in Example 1 were cut into nine slabs with dimensions of 44×10×1 mm. Coating compositions A (see Example 1) and B were each coated on 3 slabs by immersion for a few seconds followed by allowing the coating composition to cure for 24 hours at 25° C. in air. Three slabs were left uncoated as controls (PC control).

Biocompatibility was tested by contacting the test slabs with bovine blood and measuring clotting time and thrombus formation (identified by the protein (fibrin) and platelet adhesion).

Platelet and fibrin adhesion was measured by optical microscopy (OM) at 20X, after 3 and 7 min of blood contact. The results are summarized in Table 3 and 4.

TABLE 3

Clotting Time.

| Substrate | Average Clotting Time (% of control) |
|---|---|
| Test sample (PC) with coating composition A | 191 |
| Test sample (PC) with coating composition B | 203 |
| Test sample (PC) Control | 100 |

The results from Examples 1 and 2 indicated a dramatic increase in the clotting time, corresponding to a significant biocompatibility improvement, with both coatings versus the uncoated PC control. Surprisingly, clotting time was not statistically changed with coating B versus coating A, confirming that the heparin amount was too low to provoke a pharmacological anticoagulant effect. Yet, the presence of heparin did lead to a further improvement as seen by a reduction of both the platelet and fibrin adhesion and the surface covering (Table 4).

TABLE 4

OM evaluation of platelet and fibrin Adhesion.

| Material | Exposure Time (min) | Platelet/Fibrin adhesion | Surface covering % |
|---|---|---|---|
| Test sample (PC) Control | 3 | 1 | 1 |
| Test sample (PC) Control | 7 | 4 | 4 |
| Test sample (PC) with coating composition A | 3 | 0 | 0 |
| Test sample (PC) with coating composition A | 7 | 2 | 2 |
| Test sample (PC) with coating composition B | 3 | 0 | 0 |
| Test sample (PC) with coating composition B | 7 | 1 | 1 |

Surface Covering
0 = 0–1%
1 = 1–5%
2 = 5–10%
3 = 10–60%
4 = 60–80%
5 = 80–100%
Platelet & Fibrin Adhesion
0 = none
1 = discrete
2 = moderate
3 = marked
4 = severe That which is claimed is:

1. A medical device having a biocompatible coating, said biocompatible coating comprising the reaction product of a composition comprising a reactive polysiloxane, an acetoxysilane crosslinking agent, a reinforcing silica and a metal catalyst.

2. The medical device according to claim 1 wherein the reactive polysiloxane is a silanol terminated polydimethylsiloxane.

3. The medical device according to claim 1 wherein the reactive polysiloxane is a polydimethylsiloxane gum.

4. The medical device according to claim 1 wherein the composition also comprises a diluent.

5. The medical device according to claim 4 wherein the diluent is hexamethyldisiloxane.

6. The medical device according to claim 4 wherein the diluent is present in a range of between about 85 to 99 wt. % based on the weight of the total composition.

7. The medical device according to claim 1 wherein the composition also comprises an anticoagulant.

8. The medical device according to claim 7 wherein the anticoagulant is heparin and the heparin is present in a range of between about 10 ppm and 1 wt. % based on the weight of the final composition.

9. The medical device according to claim 8 wherein the heparin is in the form of a salt selected from the group consisting of ammonium, benzalkonium, calcium, lithium, and zinc.

10. The medical device according to claim 8 wherein the heparin is in the form of heparin-like polyanions selected from dermatan sulfate, heparan sulfate and their derivatives.

11. The medical device according to claim 1 wherein the composition also comprises an anticoagulant selected from the group consisting of a prostaglandin, urokinase, streptokinase, tissue plasminogen activator and hirudin.

12. The medical device according to claim 1 wherein the medical device comprises polycarbonate.

13. The medical device according to claim 1 wherein the biocompatible coating has a thickness of 0.1 to 10 micrometers.

14. A medical device having a biocompatible coating, said biocompatible coating comprising the reaction product of a composition comprising:

(A) a silanol terminated polydimethylsiloxane;
(B) an acetoxysilane crosslinking agent of the structure $$R^2_{4-b}SiR^3_b$$

in which $R^2$ is a monovalent hydrocarbon group having up to 20 carbon atoms or a phenyl group, $R^3$ is an acetoxy group, and b is 2, 3, or 4, or the hydrolysis and condensation products of these silanes;

(C) a reinforcing silica; and
(D) a metal catalyst.

15. A method of rendering a medical device more biocompatible comprising applying a biocompatible coating comprising the reaction product of a composition comprising a reactive polysiloxane, an acetoxysilane crosslinking agent, a reinforcing silica and a metal catalyst.

16. A method of rendering a medical device more biocompatible comprising:

applying a coating composition comprising a reactive polysiloxane, an acetoxysilane crosslinking agent, a reinforcing silica and a metal catalyst onto the medical device; and curing the coating composition.

* * * * *